United States Patent
Gochar, Jr.

(10) Patent No.: US 6,384,421 B1
(45) Date of Patent: May 7, 2002

(54) VISION SYSTEM FOR INDUSTRIAL PARTS

(75) Inventor: Joseph P. Gochar, Jr., Baltimore, MD (US)

(73) Assignee: Logical Systems Incorporated, Baltimore, MD (US)

( * ) Notice: Subject to any disclaimer, the term of this patent is extended or adjusted under 35 U.S.C. 154(b) by 0 days.

(21) Appl. No.: 09/411,674

(22) Filed: Oct. 7, 1999

(51) Int. Cl.$^7$ .......................... B07C 5/342; G01N 21/00
(52) U.S. Cl. .............. 250/559.46; 250/223 R; 356/428; 356/238.1; 209/563; 700/127; 702/40
(58) Field of Search .................. 250/208.1, 223 R, 250/223 B, 559.46, 559.08, 559.07, 559.05; 356/238.1, 428, 430; 702/40; 700/127; 209/524, 526, 536, 538, 548, 563, 576, 577, 587, 588, 651, 655, 701, 939; 438/125, 127, 128, 131, 132

(56) References Cited

U.S. PATENT DOCUMENTS

| | | | |
|---|---|---|---|
| 4,196,811 A | | 4/1980 | Pilesi et al. |
| 4,308,959 A | * | 1/1982 | Hoover et al. ............. 209/563 |
| 4,394,683 A | * | 7/1983 | Liptay-Wagner et al. ... 348/128 |
| 4,709,800 A | | 12/1987 | Olsen |
| 4,882,498 A | | 11/1989 | Cochran et al. |
| 4,915,237 A | * | 4/1990 | Chang et al. ............. 209/524 |
| 4,924,107 A | | 5/1990 | Tucker |
| 4,946,025 A | | 8/1990 | Murphy |
| 4,972,093 A | | 11/1990 | Cochran et al. |
| 5,051,825 A | | 9/1991 | Cochran et al. |
| 5,068,799 A | * | 11/1991 | Jarrett, Jr. .................... 702/40 |
| 5,072,127 A | | 12/1991 | Cochran et al. |
| 5,095,204 A | | 3/1992 | Novini |
| 5,172,005 A | | 12/1992 | Cochran et al. |
| 5,303,811 A | | 4/1994 | Haley |
| 5,331,151 A | | 7/1994 | Cochran et al. |
| 5,365,084 A | | 11/1994 | Cochran et al. |
| 5,440,385 A | | 8/1995 | Fein et al. |
| 5,451,773 A | | 9/1995 | Triner et al. |
| 5,572,433 A | * | 11/1996 | Falconer et al. ............. 700/127 |
| 5,581,074 A | | 12/1996 | Yoshida |
| 5,591,462 A | | 1/1997 | Darling et al. |
| 5,592,286 A | | 1/1997 | Fedor |
| 5,695,302 A | | 12/1997 | Hilbish |
| 5,699,152 A | | 12/1997 | Fedor et al. |
| 5,745,593 A | | 4/1998 | Wahawisan et al. |
| 5,805,279 A | | 9/1998 | Palombo et al. |
| 5,911,003 A | | 6/1999 | Sones |
| 5,936,353 A | | 8/1999 | Triner et al. |

FOREIGN PATENT DOCUMENTS

| | | |
|---|---|---|
| EP | 0572336 | 12/1993 |
| GB | 2005826 | 4/1979 |
| GB | 2066455 | 7/1981 |
| GB | 2078948 | 1/1982 |
| GB | 2136954 | 9/1984 |
| JP | 11108853 | 4/1999 |

OTHER PUBLICATIONS

*Inspector Product Literature*, IC Vision, Feb. 22, 2001, 16 pages.
*British Search Report*, May 16, 2001, 1 page.

* cited by examiner

Primary Examiner—Stephone Allen
(74) Attorney, Agent, or Firm—Wood, Herron & Evans, L.L.P.

(57) ABSTRACT

A machine vision inspection system for industrial parts such as plastic molded caps or the like can reliably detect defects at very high inspection rates on the order of 1600 per minute of a variety of cap colors and liners including previously difficult to inspect combinations. Advantageously, the system includes an inclined inspection ramp which provides separation between the caps which are processed through an inspection station to provide accurate imaging of each individual cap without interference from adjacent caps. Further, the inspection station includes a light source which is provided on the back side of the cap in the form of an infrared LED strobe light which provides accurate and reliable lighting for appropriate imaging of caps of any color to detect and identify defects therein.

28 Claims, 2 Drawing Sheets

VISION SYSTEM FOR INDUSTRIAL PARTS

BACKGROUND OF THE INVENTION

This invention relates to article inspection systems and, particularly, to vision systems for inspecting work pieces such as plastic molded closure caps for containers and the like.

During the manufacture of many parts such as plastic molded closure caps, a number of defects in the closure cap may exist which should cause the cap to be rejected. Commonly, closure caps of this type have a liner inserted therein against the inner surface of an end wall of the cap. Typically, the cap has a skirt projecting annularly from the peripheral rim of the end wall and the skirt may include a closure or sealing mechanism such as threads for cooperation with mating threads around the neck of a bottle, container or the like. Examples of defects in such closure caps include a liner which is positioned off center within the closure, a missing liner, a malformed liner (commonly referred to as a "moon-cut" liner), a cap which is asymmetric or off-round, a cap having an edge broken or flashing on the edge from extraneous plastic material, a pull tab defect on the liner or other similar problems. Such flaws or defects are sometimes produced during the manufacturing process. and/or as a result of contamination or damage after manufacture, but prior to the filling of the container.

Machine vision systems represent one technology for acquiring or sensing an image of at least a selected portion of a work piece, such as a cap as previously described, through an electronic sensor or camera. The image generated by the camera is then analyzed by a computer program for one or more of the above-described defects. Vision systems are commonly used to determine the existence of any marks or defects in the image of the cap and the acceptability of any such marks or defects by use of a vision computer as described.

While human vision may out perform its automatic equivalent in the ability to analyze very complex, everyday scenes, when it comes to repeated tasks, such as the inspection of plastic molded caps over and over again, a human observer understandably tires, loses concentration and makes mistakes. Machine vision inspection of such articles is known to provide some important advantages, including sophisticated image processing/analysis, repeatable performance, image acquisition for diagnosis and set up, ability to inspect a variety of articles in large tolerance and required part placement. Moreover, at inspection rates of up to 1600 parts per minute or more, each part or cap spends on the order of 33 milliseconds at an inspection station. At such speeds, only a machine vision system is fast enough to reliably and repeatedly inspect such articles.

While known vision systems have the above-described advantages for inspecting articles such as plastic molded caps and the like, they do have specific and significant limitations. Vision systems typically rely on television or video cameras to image the article to be inspected and detect any flaws. The resolution of the camera, or its ability to detect a flaw, is directly related to its ability to capture an accurate and reliable image of each individual cap, article or similar item. Typically, plastic molded caps, for example, are manufactured by the tens of thousands and each individual cap must be inspected by the vision system for quality control purposes. The large volume of caps are typically gathered in an accumulated mass and, at best, are similarly oriented on a flat surface. For accurate vision inspection and detection of flaws, the vision system must be able to precisely and accurately produce an image of each individual cap without interference from the surrounding environment or other caps.

Furthermore, inspection rates required of such systems mandate that the individual images be serially produced, analyzed and acted upon accordingly for each individual cap, once again without interference, for accurate detection of relatively small flaws or problems.

Additionally, plastic molded caps are commonly made in the wide range of colors and lining materials depending on a particular manufacturer's packaging requirements, marketing scheme or other such demands. As such, industrial vision systems should be capable of inspecting any and all such cap colors with equal accuracy, precision, efficiency and speed. However, because of the limitations in known vision systems with respect to the video cameras and lighting requirements, specific colors, such as white caps with white or foil liners or other light colors, are not accurately inspected for all possible defects. Specifically, known vision systems require a visual contrast between the cap and the liner to accurately inspect for the presence of defects such as off-center, missing or moon-cut liners within the cap.

Another problem with known vision systems involves the presence of foil or similar liners in the caps that tend to reflect light. Commonly, the caps and liners are illuminated or lighted from above to produce an image for inspection. However, foil liners and other reflective materials produce a glare when the light impinges thereon. The glare significantly reduces the clarity of the image of the cap and liner being inspected and thereby significantly reduces the accuracy and reliability of the inspection system.

SUMMARY OF THE INVENTION

The present invention provides a machine vision inspection system for inspecting work pieces such as caps and other articles and an associated method for doing so which overcomes the above-stated and other limitations with known systems/methods.

In a presently preferred embodiment, this invention is an inspection system for inspecting each of a series of serially fed work pieces in a stream of work pieces, such as plastic molded caps or the like. The system includes a feed conveyor to serially feed the caps or work pieces, each of which is typically in contact with adjacent work pieces on the feed conveyor in an accumulated mass or the like. The feed conveyor advances the caps to an inspection ramp which in a presently preferred embodiment is inclined between 35° and 50°, and most preferably at 40° with respect to a horizontal plane. The inspection ramp has a reduced friction upper surface upon which the caps or other articles advance downwardly from a top end of the inspection ramp toward a bottom end. An optional discharge conveyor is located at the bottom end of the inspection ramp to receive and discharge each of the caps for collection, packaging and/or further processing.

Advantageously, the inspection ramp is inclined so that as the caps which are in contact with one another and therefore difficult for a vision system to accurately inspect and discriminate at a top end of the ramp advance by gravity along the reduced friction surface through an inspection station located between the top and bottom ends of the ramp. The incline of the ramp produces a separation distance between each of the caps so that each cap can be individually and accurately inspected at the inspection station for defects or the like. Preferably, a pair of spaced guide rails are positioned on the lateral sides of the caps to provide for accurate lateral positioning of the caps with respect to the inspection station on the ramp.

The inspection station in a presently preferred embodiment includes an inspection window in the ramp, an infrared or other color LED strobe light source and a camera. The light source is preferably located on a back side of the inspection ramp to project light through the inspection window to back-light and illuminate each of the caps as they pass above the window. Back-lighting of the caps avoids the above-described problem of glare from foil caps and likewise offers a contrasting image even with white caps and white liners for accurate imaging. The inspection window and light source are preferably aligned with the camera which is located on a top side of the inspection ramp and oriented generally perpendicularly with respect to the inspection ramp at the inspection station. Preferably, the positioning of the light source, inspection window and camera provides for a full and complete image of the cap for accurate resolution and detection of possible defects in the cap.

The system also includes a processing unit such as a computer or the like operably coupled to the camera to analyze the images of the caps generated by the camera with respect to predetermined quality control standards. For example, specific defects as described hereinabove, if detected by the camera, are outside of the predetermined quality control standards utilized by the computer to analyze each of the images generated by the camera. If a particular cap fails the predetermined quality control standards, a rejection mechanism, typically an air jet or the like, is coupled to the processing unit to receive a control signal from the. processing unit and, if such a signal is received by the air jet or other rejection mechanism, the identified cap is then removed from the stream by the air jet or other rejection mechanism. The rejected cap is then discarded, analyzed or recycled as is appropriate.

This invention in a presently preferred embodiment overcomes the above-described disadvantages of known vision inspection systems by accurately and reliably providing a separation distance between each of the serially fed work pieces, articles, caps or the like to be inspected as a result of the inspection ramp and the inclination thereof. Further, the processing or inspection rate is not diminished as a result of the orientation and configuration of the inspection ramp and inspection station components thereby providing inspection rates as high as 1600 per minute or more depending upon the size of the items being inspected and other operational requirements.

Furthermore, heretofore difficult to inspect or analyze materials such as white and other light colored plastic molded caps and liners are reliably and effectively illuminated for accurate imaging and detection by the camera and processing unit because of the opportunity for back lighting the cap with an infrared or other color LED strobe light source.

BRIEF DESCRIPTION OF THE DRAWINGS

The objectives and features of the invention will become more readily apparent from the following detailed description taken in conjunction with the accompanying drawings in which.

DETAILED DESCRIPTION OF THE INVENTION

Figure 1:
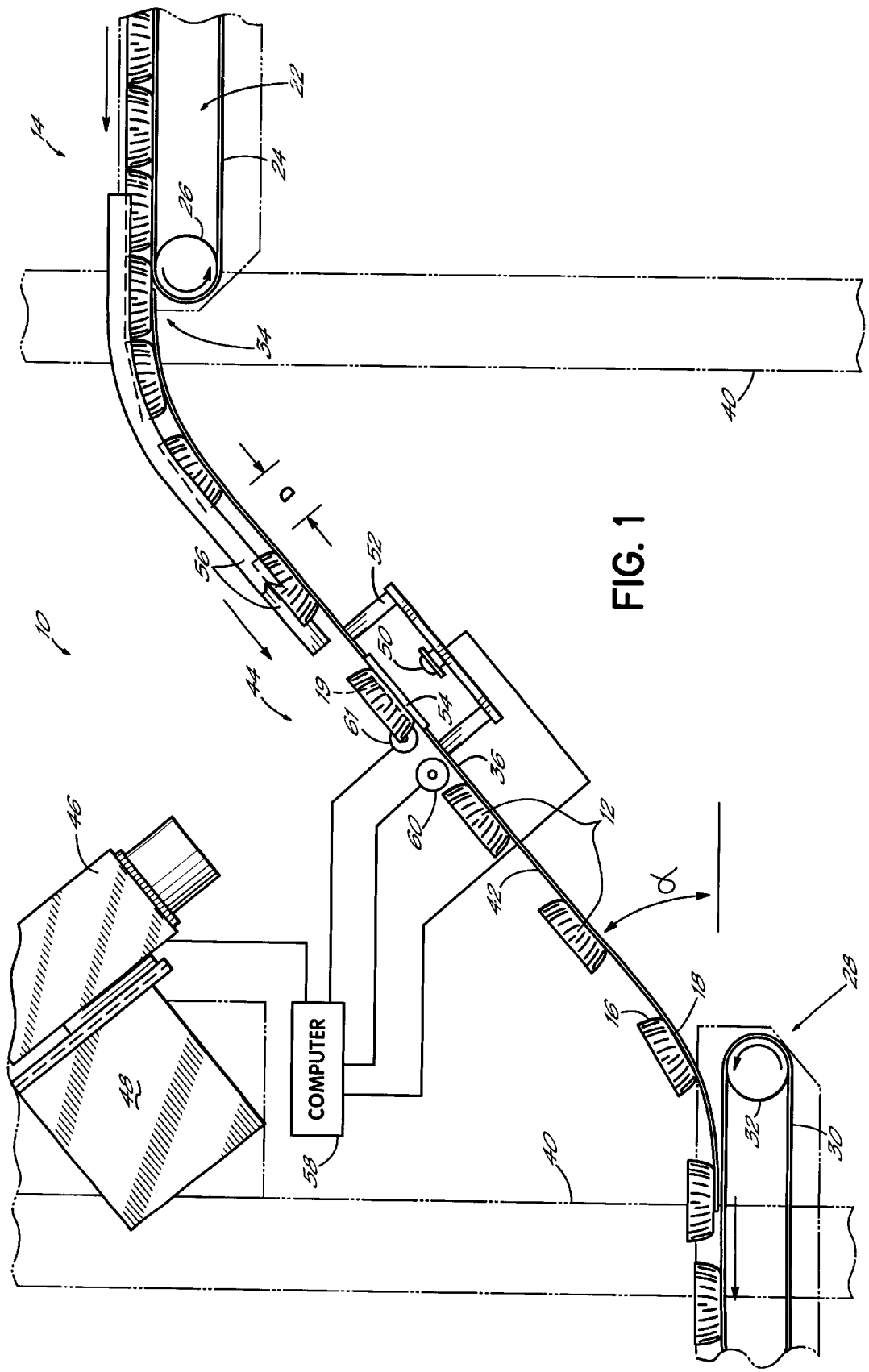
FIG. 1 is a schematic representation of a presently preferred embodiment of the vision inspection system according to this invention.

Referring to FIG. 1, a presently preferred embodiment of a vision inspection system and associated method for industrial parts 12 is shown. The system 10 in a presently preferred form is utilized to inspect each of a series of serially fed work pieces in a stream of work pieces for defects or the like. The work pieces or industrial parts 12 may be any one of a variety of items such as plastic molded caps as shown in FIG. 1. Commonly, the caps 12 are produced in an injection molding or similar process (not shown) and discharged in a batch 14 or large quantities to the system 10. The caps include a peripheral skirt 16 projecting from a base or end wall 18 and a liner 19 may be inserted into the cap 12.

As shown in FIG. 1, the vision system 10 includes a feed conveyor 22 having a belt 24 trained for travel around a pair of rotating rollers 26 (only one of which is shown in FIG. 1), at least one of which is driven to provide rotation for the feed conveyor 22. Similarly, a discharge conveyor 28 is provided with a belt trained 30 around a pair of rollers 32 (only one of which is shown in FIG. 1), at least one of which is driven. As shown in FIG. 1, a batch 14 of caps 12 is preferably delivered to a top end 34 of an inclined inspection ramp 36 by the feed conveyor 22. Similarly, the caps 12 are discharged at a bottom end of the inspection ramp 36 onto the discharge conveyor 28 for subsequent processing, packaging or the like. Alternatively, the inspection ramp or platform 36 may be generally horizontal in one preferred embodiment of this invention. Commonly, the work pieces or caps 12 are accumulated together in the batch 14 or the like on the feed conveyor 22 at the top end 34 of the inspection ramp 36 such that each cap 12 is in very close proximity to, if not in touch or contact with, adjacent caps 12 as shown in FIG. 1. The inspection ramp 36 and conveyors 22, 28 are supported by appropriate support posts 40 and other structure as will be necessary for the particular arrangement, configuration and environment required for the vision system 10 as is readily understood by one of ordinary skill in the art.

The delivery rate or speed of the feed conveyor 22 depends upon the required inspection rate for the caps 12, the size of the caps 12 and other relevant factors. For example, if the caps 12 being inspected have a diameter of 1.1 inches and an inspection rate of 1600 per minute is required, the feed conveyor 22 will operate at about 1763 inches per minute maximum speed for delivery of the caps 12 to the top end 34 of the inspection ramp 36. Preferably, the inspection ramp 36 is inclined at angle a between 35° and 50° with respect to a horizontal plane and, most preferably, approximately 40° in a presently preferred embodiment. The inspection ramp 36 has an upper surface 42 upon which the caps 12 slide by gravity from the top end 34 toward the bottom end 38 thereof. The upper surface 42 of the ramp 36 is preferably a reduced friction surface and may be constructed of polished stainless steel or include a coated Teflon layer or the like. Alternatively, the ramp 36 may be constructed from UHM polyethylene and/or be made of a clear or translucent material to allow the transmission of light therethrough as will be described later herein.

Moreover, the top end 34 of the ramp 36 is curved as to avoid separation of the caps 12 from the upper surface 42 of the ramp 36 as the caps 12 move thereon. The shape of the top end 34 is most preferably a parabola, but may be arcuate or a chord of a circle with a five inch or more radius to maintain cap 12 contact therewith.

Positioned intermediate the top end 34 and bottom end 38 of the inspection ramp 36 is an inspection station 44 which includes a camera 46 mounted preferably generally perpendicularly with respect to the surface 42 of the ramp 36 on an upper side thereof. In a presently preferred embodiment, the camera 46 is a CCD progressive scan type camera which is readily available from many sources. Appropriate support posts and mounting 48 structure is preferably provided for the camera 46 for adjustably positioning the camera 46 a predefined distance from the ramp 36.

The inspection station 44 also includes a light source 50 preferably mounted on a support frame 52 on a back surface of the inspection ramp 36 and in-line with the viewing axis of the camera 46 to back light the cap 12 to produce an image of the cap 12 by the camera 46. In a presently preferred embodiment, the light source 50 is an infrared or other color LED strobe light which is preferably adjustable to provide a frequency as is appropriate for the inspection rate of the caps 12, typically as high as 1600 per minute depending on the size of the caps being inspected and other system 10 requirements. Some CCD cameras include an infrared cut filter installed by the manufacturer. If such is the case and an IR light source is used with this system, this filter must be removed. The light source 50 is most preferably in line with the camera 46 and on the opposite side of the cap 12 at the inspection station. However, the light source 50 may be alternatively positioned while providing back light to the cap 12 for the camera 46 within the scope of this invention. Alternatively, the light source 50 may be provided proximate the upper surface 42 of the ramp 36 for top lighting of the caps 12 in addition to or as a substitute for the back light source as shown in FIG. 1.

An inspection window 54 which is preferably transparent, translucent or the like so that at least some light may pass therethrough to illuminate the cap 12 may be provided at the inspection station 44 in line with the camera 46 and the light source 50 if the inspection ramp 36 is not made of a translucent, transparent or similar material. The inspection window 54 preferably produces a high diffusion of the light and may be opal glass. The spacing of the light source 50 from the cap 12 being inspected at the inspection station 44 and the spacing of the camera 46 from the cap 12 is dependent upon the diameter of the cap and the size of the lens being utilized within the camera 46. Preferably, the spacing is optimized to fully illuminate the cap 12 while providing a full size image of the cap 12 in the field of view of the camera 46.

As the caps 12 are delivered to the top end 34 of the ramp 36, a separation distance D between the adjacent caps is created by guiding the caps 12 onto the ramp 36 that is inclined preferably at 40°. The shape of the ramp 36 and the velocity that the caps 12 are loaded onto the ramp 36 helps to ensure that the caps 12 remain in contact with the ramp 36 as they advance downwardly. Maintaining contact with the ramp 36 is an important aspect of this invention since the caps 12 must be perpendicular to the center line of the camera 46 when the image is taken for inspection purposes. The caps 12 accelerate down the ramp 36 due to gravity and the reduced friction surface 42 thereby generating the distance or spacing D between the adjacent caps 12. Separation between the caps 12 being inspected is important to provide an accurate image and subsequent analysis of each individual cap 12 without interference from the adjacent caps. Preferably, a pair of spaced guides 56 are provided at least on the upper portion of the inspection ramp 36 to maintain accurate lateral positioning between the guides 56 for the caps 12 traveling down the ramp 36 so that the caps 12 can be accurately positioned at the inspection station 44 for proper imaging by the camera 46.

Backlighting of the caps 12 by the light source 50 in many instances allows for better contrast and image quality by the vision system 10. An infrared light source 50 provides increased imaging capabilities for particular colors of caps 12, for example white caps with white liners, which with previously known vision systems are difficult to accurately inspect.

The image produced by the camera 46 of each individual cap 12 is conveyed to a computer 58 or a processing unit electrically and operably coupled to the camera 46. As with known vision systems, the processing unit or computer 58 analyzes each of the images generated by the camera 46 with respect to predetermined quality control standards to detect possible defects or problems with each cap 12, such as an off-center or missing liner, a moon-cut liner, a cap which is not properly formed or similar defects. Preferably, a trigger 61 in the form of a photo-electric eye or the like is operably coupled to the computer 58 and camera 46 to detect the leading edge of the cap 12 when it is positioned on the inspection window 54. When the cap 12 is detected by the trigger 61, a signal is sent to the camera 46 and light 50 to take a picture or image of the cap 12 for inspection and analysis by the computer 58. If the computer 58 determines that the cap 12 has any one of a number of identifiable defects, a control signal is sent from the computer or processing unit 58 to a rejection mechanism 60 coupled thereto. The rejection mechanism 60 may be any one of a number of items designed to remove the identified cap 12 from a stream of caps. For example, an air jet 60 as shown in FIG. 1 may be positioned immediately below or at another position downstream from the inspection station 44 so as to produce upon receipt of the appropriate control signal a puff of air to force the cap 12 off of the ramp 36 and out of the stream for further inspection, discharge, recycling or the like. As such, when the processing unit 58 is unable to identify a defect in the cap 12, the cap 12 proceeds to the bottom end 38 of the inspection ramp 36 and onto the discharge conveyor 28 for further processing, packaging or the like.

Figure 2:
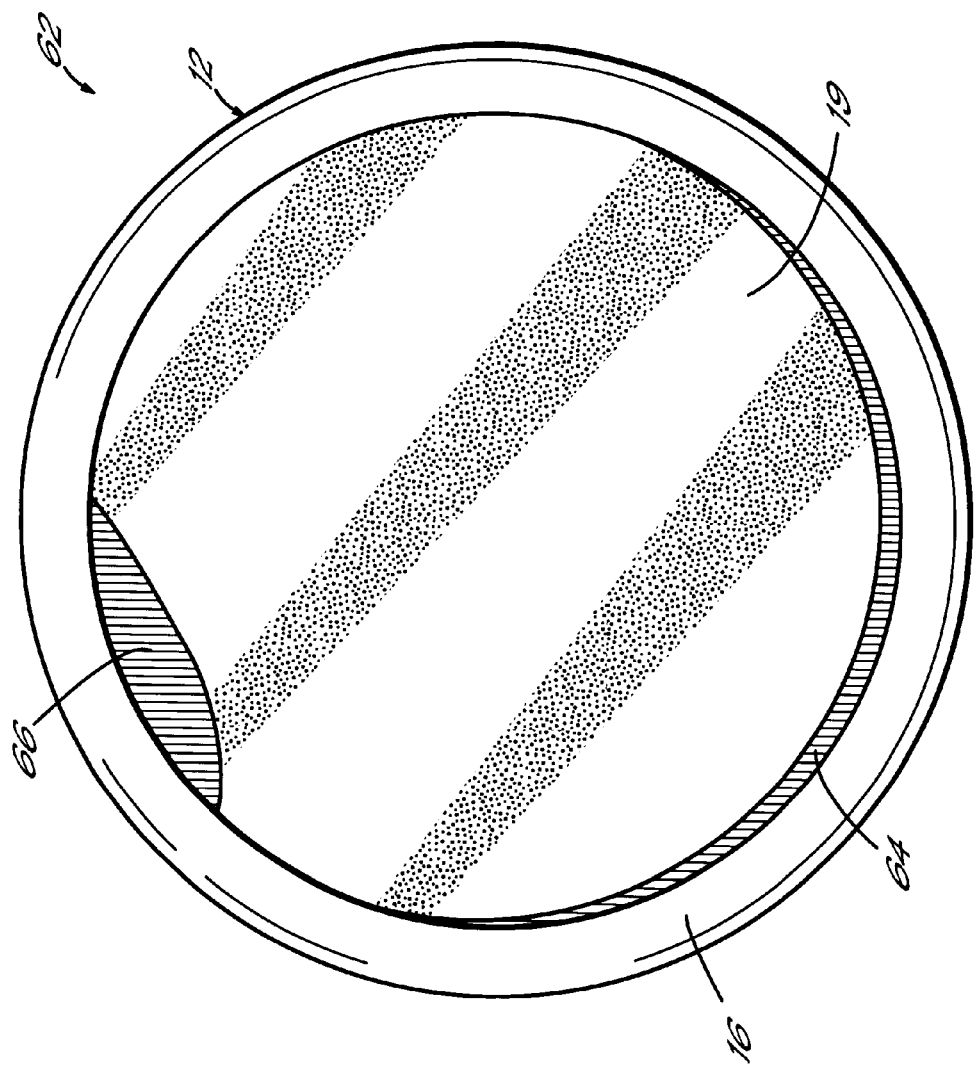
FIG. 2 is a schematic representation of an image of a plastic molded cap produced by the system.

Referring to FIG. 2, a schematic representation of an image 62 of a cap 12 and liner 19 produced according to the system 10 of FIG. 1 is shown. The image 62 was produced from an IR LED light source 50 of a 38 mm white cap 12 with the a white liner 19 positioned off-center therein as shown by the gap 64 between the liner 19 and the skirt 16. Additionally, the liner 19 has a moon-cut defect 66. As a result of the off-center position of the liner 19 and/or the moon-cut defect 66, the cap of FIG. 2 was rejected by the system 10.

From the above disclosure of the general principles of the present invention and the preceding detailed description of at least one preferred embodiment, those skilled in the art will readily comprehend the various modifications to which this invention is susceptible. Therefore, I desire to be limited only by the scope of the following claims and equivalents thereof.

I claim:

1. An inspection system for inspecting each of a series of serially feed work pieces in a stream of work pieces, the inspection system comprising:

an inspection ramp inclined downwardly with respect to a horizontal plane and having a top end and a bottom end, each of the work pieces being serially received at the top end and discharged at the bottom end, each of the work pieces separating a distance from the adjacent work pieces and maintaining contact with an upper surface of the inspection ramp as it moves from the top end to the bottom end;

wherein the upper surface of the inspection ramp is generally planar and stationary;

an inspection station located intermediate the top end and the bottom end of the inspection ramp, the inspection station including a light source and a camera, the light source being positioned to illuminate each of the work pieces at the inspection station for imaging by the camera;

a processing unit operably coupled to the camera to analyze images of the work pieces generated by the camera with respect to predetermined quality control standards; and a rejection mechanism operably coupled to the processing unit to receive a control signal from the processing unit, the rejection mechanism being operable to remove selected work pieces from the stream based on the control signal.

2. The inspection system of claim 1 wherein the inspection ramp is inclined between about 35° and about 50° with respect to the horizontal plane.

3. The inspection system of claim 1 further comprising:
a feed conveyor in communication with the top end to serially feed the work pieces each of which is in contact with adjacent work pieces on the feed conveyor; and
a discharge conveyor in communication with the bottom end to receive and discharge each of the work pieces at the bottom end.

4. The inspection system of claim 1 further comprising:
a pair of spaced guides to maintain lateral alignment of the work pieces as they move on the inspection ramp.

5. The inspection system of claim 1 further comprising:
a trigger operably coupled to the camera and positioned relative to the inspection station to detect a position of the work piece and send a trigger signal to the camera to take an image of the work piece.

6. The inspection system of claim 1 wherein the light source is positioned on a back side of the work piece and opposite from the camera to back light the work piece and at least a portion of the inspection ramp at the inspection station is at least translucent to permit light from the light source to pass therethrough and illuminate the work piece.

7. The inspection system of claim 1 wherein the light source is an LED strobe infrared light source.

8. The inspection system of claim 1 wherein the movement of the work pieces on the inspection ramp is controlled primarily by gravity.

9. The inspection system of claim 1 wherein the camera is positioned generally perpendicularly with respect to the inspection ramp at the inspection station.

10. The inspection system of claim 1 wherein the top end of the inspection ramp is curved so that the work pieces maintain contact with the upper surface of the ramp while moving thereon.

11. The inspection system of claim 1 wherein the light source illuminates at least an interior portion of the image contained within a perimeter of the work piece.

12. An inspection system for inspecting each of a series of serially feed work pieces in a stream of work pieces, the inspection system comprising:
a feed conveyor to serially feed the work pieces each of which is in contact with adjacent work pieces on the feed conveyor;
an inspection ramp inclined between 35° and 50° with respect to a horizontal plane and having a reduced friction surface, a top end and a bottom end and being in communication with the feed conveyor to serially receive each of the work pieces at the top end and discharge each work piece at the bottom end, each of the work pieces separating a distance from the adjacent work pieces and maintaining contact with the reduced friction surface as it moves by gravity from the top end to the bottom end of the inspection ramp;
a pair of spaced guides to maintain lateral alignment of the work pieces as they move on the inspection ramp;
a discharge conveyor in communication with the inspection ramp to receive and discharge each of the work pieces at the bottom end;
an inspection station located intermediate the top end and the bottom end of the inspection ramp, the inspection station including an inspection window in the inspection ramp, an infrared LED strobe light source and a camera, the light source being located on a back side of the inspection ramp and aligned with the inspection window and the camera and the camera being located on a top side of the inspection ramp and oriented generally perpendicularly with the inspection ramp at the inspection station;
a trigger operably coupled to the camera and positioned relative to the inspection station to detect a position of the work piece and send a trigger signal to the camera to take an image of the work piece;
a processing unit operably coupled to the camera to analyze images of the work pieces generated by the camera with respect to predetermined quality control standards; and
a rejection mechanism operably coupled to the processing unit to receive a control signal from the processing unit and the rejection mechanism being operable to remove selected work pieces from the stream based on the control signal.

13. A method of inspecting each of a series work pieces, the method comprising the steps of:
feeding the work pieces to a top end of a downwardly inclined inspection ramp, wherein each of the work pieces is in contact with an adjacent work piece at the top end;
moving each of the work pieces downwardly along the inspection ramp toward a bottom end of the inspection ramp;
generating a spacing distance on the inspection ramp between each of the work pieces and adjacent work pieces;
illuminating each of the work pieces with a light source;
producing an image of each work piece illuminated by the light source without interference from the adjacent work pieces;
analyzing the image with respect to predetermined quality control standards;
removing selected ones of the work pieces based upon the analyzing step; and
discharging a remainder of the work pieces.

14. The method of claim 13 wherein the moving of the work pieces downwardly along the inspection ramp is accomplished by gravity and the inspection ramp is generally stationary.

15. The method of claim 14 wherein an upper surface of the inspection ramp is generally planar.

16. A method of inspecting each of a series work pieces, the method comprising the steps of:
feeding the work pieces to an inspection platform;

illuminating each of the work pieces with a light source;

producing an image with a camera of each work piece illuminated by the light;

wherein the image includes at least an interior portion of the work piece within a perimeter of the work piece;

wherein the illuminating further comprises back lighting the work pieces from a position generally opposite from the camera, at least a portion of the inspection platform is at least translucent to permit passage of light from the light source through the inspection platform to illuminate the work pieces;

analyzing the image with respect to predetermined quality control standards;

removing selected ones of the work pieces based upon the analyzing step; and discharging a remainder of the work pieces.

17. The method of claim 16 wherein an infrared light source is used to illuminate the work pieces.

18. An inspection system for inspecting each of a series of serially feed work pieces in a stream of work pieces, the inspection system comprising:

an inspection ramp inclined downwardly with respect to a horizontal plane and having a top end and a bottom end, each of the work pieces being serially received at the top end and in contact with an adjacent work piece, each work piece being discharged at the bottom end, each of the work pieces separating a distance from the adjacent work pieces and maintaining contact with an upper surface of the inspection ramp as it moves from the top end to the bottom end, the upper surface of the inspection ramp being generally planar and stationary so that the movement of the work pieces on the upper surface is controlled primarily by gravity;

an inspection station located intermediate the top end and the bottom end of the inspection ramp, the inspection station including a light source and a camera, the light source being positioned to illuminate each of the work pieces at the inspection station for imaging by the camera;

a processing unit operably coupled to the camera to analyze images of the work pieces generated by the camera with respect to predetermined quality control standards; and a rejection mechanism operably coupled to the processing unit to receive a control signal from the processing unit, the rejection mechanism being operable to remove selected work pieces from the stream based on the control signal.

19. The inspection system of claim 18 further comprising:

a trigger operably coupled to the camera and positioned relative to the inspection station to detect a position of the work piece and send a trigger signal to the camera to take an image of the work piece.

20. The inspection system of claim 18 wherein at least a portion of the inspection platform at the inspection station is at least translucent to permit light from the light source to pass therethrough and illuminate the work piece.

21. The inspection system of claim 18 wherein the light source is an infrared light source.

22. The inspection system of claim 21 wherein the infrared light source is an infrared LED strobe.

23. A method of inspecting each of a series of plastic molded caps each having a liner therein, the method comprising the steps of:

feeding the caps to a top end of a downwardly inclined inspection ramp, wherein each of the caps is in contact with an adjacent cap at the top end;

moving each of the caps downwardly along the inspection ramp toward a bottom end of the inspection ramp;

generating a spacing distance on the inspection ramp between each of the caps and adjacent caps;

illuminating each of the caps with a light source;

producing an image of each work piece illuminated by the light source without interference from the adjacent caps;

analyzing the image with respect to predetermined quality control standards;

removing selected ones of the caps based upon the analyzing step; and discharging a remainder of the caps.

24. A method of inspecting each of a series of plastic molded caps each having a liner therein, the method comprising the steps of:

feeding the caps to a top end of a downwardly inclined stationary inspection ramp, wherein the top end of the inspection ramp is curved;

wherein each of the caps is in contact with an adjacent cap at the top end;

moving each of the caps downwardly by gravity along a generally planar portion of the inspection ramp toward a bottom end of the inspection ramp;

generating a spacing distance on the inspection ramp between each of the caps and adjacent caps;

illuminating each of the caps with an infrared light source;

wherein the illuminating includes a portion of the liner within a perimeter of the cap and further comprises back lighting the caps from a position generally behind the ramp, at least a portion of the inspection ramp is at least translucent to permit passage of light from the light source through the inspection ramp to illuminate the caps;

producing an image of each work piece illuminated by the light source without interference from the adjacent caps;

analyzing the image with respect to predetermined quality control standards;

removing selected ones of the caps based upon the analyzing step; and discharging a remainder of the caps.

25. The method of claim 24 wherein the liner has a foil surface.

26. The method of claim 24 wherein at least selected caps are white.

27. An inspection system for inspecting each of a series of serially feed plastic molded bottle caps in a stream of bottle caps, the inspection system comprising:

a feed conveyor to serially feed the bottle caps each of which is in contact with adjacent bottle caps on the feed conveyor;

an inspection ramp being stationary and inclined between 35° and 50° with respect to a horizontal plane and having a reduced friction generally planar surface, a top end and a bottom end and being in communication with the feed conveyor to serially receive each of the bottle caps at the top end and discharge each bottle cap at the bottom end, each of the bottle caps separating a distance from the adjacent bottle caps and maintaining contact with the reduced friction generally planar surface as it moves by gravity from the top end to the bottom end of the inspection ramp;

wherein the top end of the inspection ramp is curved so that the bottle caps maintain contact with the upper surface of the inspection ramp while moving thereon;

a pair of spaced guides to maintain lateral alignment of the bottle caps as they move on the inspection ramp;

a discharge conveyor in communication with the inspection ramp to receive and discharge each of the bottle caps at the bottom end;

an inspection station located intermediate the top end and the bottom end of the inspection ramp, the inspection station including an inspection window in the inspection ramp, an infrared LED strobe light source and a camera, the light source being located on a back side of the inspection ramp and aligned with the inspection window and the camera and the camera being located on a top side of the inspection ramp and oriented generally perpendicularly with the inspection ramp at the inspection station;

a trigger operably coupled to the camera and positioned relative to the inspection station to detect a position of the work piece and send a trigger signal to the camera to take an image of the work piece;

a processing unit operably coupled to the camera to analyze images of the bottle caps generated by the camera with respect to predetermined quality control standards;

wherein the light source illuminates at least an interior portion of each bottle cap and the respective image includes an the interior portion; and a rejection mechanism operably coupled to the processing unit to receive a control signal from the processing unit and the rejection mechanism being operable to remove selected bottle caps from the stream based on the control signal.

28. The inspection system of claim 27 wherein the feed conveyor delivers about 1600 bottle caps per minute to the inspection ramp.

* * * * *